United States Patent [19]
Audia et al.

[11] Patent Number: 5,574,160
[45] Date of Patent: Nov. 12, 1996

[54] SYNTHEIS OF BENZOQUINOLINONES

[75] Inventors: James E. Audia; James J. Droste; Perry C. Heath; Leland O. Weigel, all of Indianapolis,, Ind.

[73] Assignee: Eli Lilly and Company, Indianapolis, Ind.

[21] Appl. No.: 443,994

[22] Filed: May 18, 1995

Related U.S. Application Data

[63] Continuation-in-part of Ser. No. 249,582, May 26, 1994, abandoned.

[51] Int. Cl.$^6$ ............................................. C07D 215/227
[52] U.S. Cl. ............................................. 546/110
[58] Field of Search ............................................. 546/110

[56] References Cited

U.S. PATENT DOCUMENTS 5,239,075  8/1993  Audia et al. ............................................. 546/110

FOREIGN PATENT DOCUMENTS 0 532 190   3/1993   European Pat. Off. ............... 546/110
0 564 193  10/1993   European Pat. Off. ............... 546/110

OTHER PUBLICATIONS

Audia, et al., *Tetrahedron Letters*, 34, 7001–7004 (1993).
Evans, David A, *J. Am. Chem. Soc.*, 92, 7593–7595 (1970).
Fraser, et al., *Tetra. Lett.*, 41, 3929–3932 (1979).
Volpe, et al., *Tetra. Lett.*, 28 (21), 2367–2370 (1987).
Paulvannan, et al., *J. Org. Chem.*, 57, 5319–5328 (1992).
Eldin, et al., *J. Org. Chem.*, 58, 3490–3495 (1993).
d'Angelo, et al., *Tetra. Asymmetry.*, 1(4), 459–505 (1992).
Polniaszek, et al., *Synthetic Commun.*, 22(1), 171–178 (1992).
d'Angelo, et al., *Tetra. Lett.*, 29, 4427–4430 (1988).

*Primary Examiner*—Zinna Northington Davis
*Attorney, Agent, or Firm*—Joseph A. Jones; David E. Boone

[57] ABSTRACT

A 1-pot process for preparing 10*b*-methyl-3-oxo-benzo[f] quinolines.

15 Claims, No Drawings

SYNTHESIS OF BENZOQUINOLINONES

CROSS-REFERENCE

This application is a continuation-in-part of U.S. application Ser. No. 08/249,582, filed May 26, 1994, now abandoned.

FIELD OF THE INVENTION

The present invention belongs to the fields of organic chemistry, pharmaceutical chemistry and chemical manufacture, and provides a convenient and economical process for preparing benzoquinolinones which are useful as 5α-reductase inhibitors, and as intermediates for the preparation of additional such pharmaceuticals.

BACKGROUND OF THE INVENTION

One of the currently active fields of pharmaceutical research is the inhibition of 5α-reductase, the enzyme which converts testosterone to dihydrotestosterone, a more potent androgen. It has been demonstrated that inhibitors of 5α-reductase can block the formation of dihydrotestosterone and ameliorate a number of highly undesirable conditions, including male pattern baldness and benign prostatic hypertrophy. Finasteride, a 5α-reductase inhibitor is now approved in the United States for the treatment of benign prostatic hyperplasia. Mocellini et al., *The Prostate*, 22, 291–99 (1993).

Audia et al., have disclosed a series of octahydrobenzo[f]quinolinones which are 5α-reductase inhibitors. See U.S. Patent 5,239,075; *Tet. Let.* 44, 7001 (1993) and *J. Med. Chem.* 36, 421 (1993). The present invention provides an improved process for the synthesis of certain of those compounds.

SUMMARY OF THE INVENTION

The present invention provides a process for preparing a compound of the formula

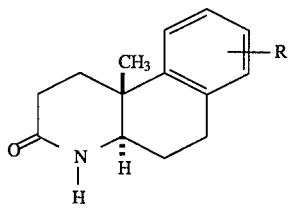

wherein R is hydrogen, methylthio, chloro, bromo or fluoro, and is located at the 7-, 8- or 9-position; comprising reacting a compound of the formula

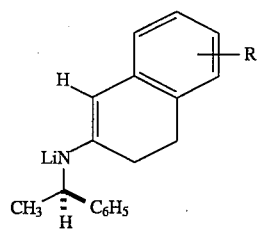

with methyl iodide in an ether solvent to prepare a compound of the formula

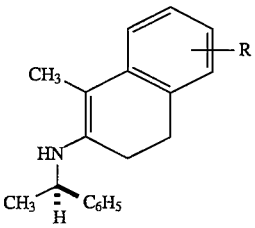

combining acrylic anhydride or acryloyl chloride with the reaction mixture comprising the compound of formula III to prepare a compound of the formula

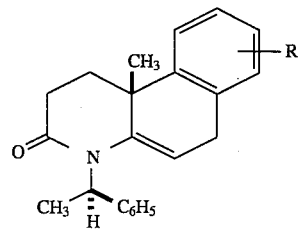

quenching the reaction with sodium bicarbonate, evaporating the organic solution comprising the compound of formula IV;

and combining the residue comprising the compound of formula IV with a trialkylsilane and trifluoroacetic acid in the absence of a solvent to prepare the compound of formula I.

DESCRIPTION OF THE PREFERRED EMBODIMENTS

Throughout the present document, temperatures will be expressed in degrees Celsius, and expressions of quantity, proportion and the like will be in weight units unless otherwise stated.

A previous synthesis of the compounds of formula I was taught in U.S. Pat. No. 5,239,075, which shows that the compounds are active as pharmaceuticals, and may also be used as intermediates for the synthesis of further pharmaceuticals by alkylating the nitrogen atom. The nitrogen atom is the 4-position of the nucleus, as shown below.

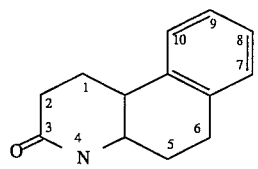

The substituent R may occupy either the 7-, 8- or 9-position of the nucleus.

Another synthesis, of which the present invention constitutes an improvement, was shown in European Patent Publication 0564193. That synthesis is the general case of the present aza-annulation step and reduction-cleavage step, lacking the refinements which link together the present steps without isolation or purification.

The present process is of the type known as "one-pot" among chemists, because all of its steps can be carried out one after the other without purification or even isolation of the intermediate products. It is, indeed, possible to carry out the process in a single reactor, or pot, although various evaporations of solvent, replacement of solvents and the like are required.

The present process is asymmetric and prepares the specific enantiomer of the compound of formula I which provides best biological activity.

Starting Material

The starting material of formula II is prepared most conveniently by a modification of a process shown in European Patent Publication 0564193. A substituted 2-tetralone, having the desired R substituent on the unsaturated ring, is reacted with (E)-(+)-phenethylamine to prepare the intermediate of the formula

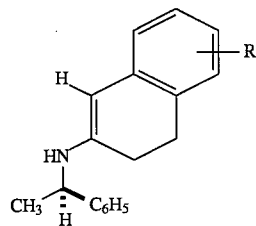

The reaction is conveniently carried out at elevated temperature, particularly the reflux temperature, in toluene in the presence of a strong acid such as p-toluenesulfonic acid. Water must be removed as it is formed in this reaction, and the absence of water being formed is an indication of completion of the reaction. A slight excess of phenethylamine, such as about 1.05–1.10 equivalents, should be used. Alternatively, tetrahydrofuran (THF) may be used as the solvent, and it is particularly convenient in that case to use molecular sieves to dehydrate the reaction mixture, using at least twice the weight of molecular sieves compared to the amount of water which will be released by the process.

The above phenethylamino compound is lithiated to prepare the starting material of formula II. The reaction may be carried out with, for example, n-butyllithium or with lithium diisopropylamide (LDA). When the reaction is carried out, as is preferred, with LDA, the best results are obtained if the LDA is freshly generated from diisopropylamine and n-butyllithium immediately before use in the process. A substantial excess, about 15–25%, of LDA should be used for best results.

The LDA reaction is best carried out in THF at a low temperature in the range of about −100° to about 0°, preferably about −78° to about −10°. The phenethylamino compound need not be purified or isolated, but the first reaction mixture should be evaporated under vacuum and the residue taken up in THF. It is preferred to add the phenethylamino material, in solution, to a solution of LDA in cold tetrahydrofuran; the opposite manner of addition is operable but provides lower yields. The reaction may be carried out in quite short periods of time, less than one hour in general.

The lithio compound of formula II is difficult to isolate and purify, and so it should be introduced into the process of the present invention as a solution in the lithiation reaction mixture.

Methyl Iodide Step

In the first step of the present process, the lithio compound of formula II is reacted with methyl iodide to provide the compound of formula III. It is advisable to use about 15–25% of excess methyl iodide, and to carry out the process in an ether solvent, such as diethyl ether, methyl butyl ether or, preferably, THF. The reaction is very rapid at low temperatures in the range of about −100° to about −50°, most preferably, about −80° to about −60°. Reaction times in the range of from about a few minutes to about one hour are adequate, and a 20-minute reaction time is often preferred.

If the compound of formula II is in the form of the reaction mixture from lithiation with LDA, and the reaction mixture therefore contains the residual diisopropylamine, that amine must be neutralized before further reaction of the compound of formula III. Most conveniently, the methyl iodide mixture is allowed to warm to a temperature close to 0°, and a sufficient amount of methanesulfonic acid is added to neutralize the diisopropylamine. Other strong acids may be used, but methanesulfonic acid is particularly convenient because the resulting methanesulfonate salt of diisopropylamine is only slightly soluble and therefore may be easily removed by simple filtration or centrifugation.

Aza-Annulation Step

The reaction mixture comprising the compound of formula III is combined with acrylic anhydride or acryloyl chloride to initiate the aza-annulation reaction which forms the compound of formula IV. It is best to generate the acrylic anhydride, the preferred reagent, immediately before use by the reaction of acryloyl chloride and acrylic acid, using triethylamine and a stabilizer, such as hydroquinone and butylated hydroxytoluene, in THF.

The aza-annulation is best carried out by adding the acrylic anhydride or acryloyl chloride at a very low temperature, such as from about −100° to about −70°, and allowing the mixture to warm very slowly with stirring to a temperature in the range of about −20° to about 0°, or even up to about 10°–20° A period of 12–15 hours is not too much for that period of time. When the reaction has gone as far toward completion as is desired, the reaction is quenched by addition of sodium bicarbonate. It is preferred to use from about 1.5 to about 4 equivalents of base, most preferably about 2 equivalents. The base may be added as a solution, for example, in water or in an aqueous solvent such as water/dimethylaminopyridine, but it is preferred to add the base in solid form. The reaction mixture is stirred with the quenching base for a brief period, and then the mixture is filtered, the volatiles are removed, and the solvent may be replaced with an ether solvent, preferably diethyl ether, and the organic solution may then be worked up by washing with aqueous base and aqueous acid, and perhaps with additional purification steps such as a wash with a saturated salt solution. If such work up steps are used, the solution is then dehydrated and evaporated under vacuum to obtain the non-volatile portions of the reaction mixture, containing the final intermediate of formula IV. On the other hand, the residue from the quenched reaction mixture may be carried on without work up if desired.

Reduction-Cleavage Step

The residue from the aza-annulation step is cooled, and a chilled mixture of a trialkylsilane and trifluoroacetic acid is added. The addition should take place at a low temperature in the range of from about −40° to about 0°, and no other solvent is used. A large quantity of trifluoroacetic acid, in the range of about 10–50 equivalents, most preferably about 20–30 equivalents is used. The preferred trialkylsilane is triethylsilane, although trimethylsilane, tripropylsilane and the like may also be used. A substantial excess of trialkylsilane, in the range of about 5–20 equivalents, most preferably about 7–15 equivalents is used. The mixture is stirred for about 10–20 hours while it is allowed to warm slowly to about 30°, and then the mixture is slowly heated to an elevated temperature, preferably the reflux temperature, and is stirred at that temperature for a few hours, such as about 2–6 hours to complete the formation of the compound of formula I.

Purification

The residue containing the product of formula I is dissolved, preferably in a haloalkane such as dichloromethane, washed with base, such as aqueous sodium bicarbonate, and concentrated under vacuum. The residue is thoroughly washed with, for example, an ether solvent which may often preferably be diethyl ether to obtain the purified desired compound of formula I.

Preferred Aspects

Certain particular details of the present process are especially preferred, and will be individually mentioned to assure that the reader understands the emphasis on them. The reader will also understand that the preferred aspects may be combined to provide further particularly preferred variations of the invention.

1) The group R is at the 8-position;
2) The group R represents bromo or chloro;
3) The group R represents methylthio;
4) The compound of Formula II is supplied as a reaction mixture containing residual diisopropylamine;
5) The solvent of the above reaction mixture is tetrahydrofuran;
6) The reaction of the compound of Formula II with methyl iodide is carried out at from about −80° to about −60°;
7 The reaction mixture from the methyl iodide step is further treated with methanesulfonic acid;
8 Acrylic anhydride is used and is made in situ;
9 The aza-annulation step is begun at from about −100° to about −70°, and is then warmed to from about −20° to about 20°;
10) The aza-annulation reaction is quenched by addition of solid sodium bicarbonate;
11) The reduction-cleavage step is begun at from about −40° to about 0°, and is then warmed slowly to the reflux temperature of the mixture.

EXAMPLES

The following examples are provided further to enlighten the reader about the present invention, and to assure that the most preferred methods of carrying out the invention are fully understood.

Preparation 1

(R)-6-bromo-2-(1-phenylethylamino)-3,4-dihydronaphthalene, lithium salt

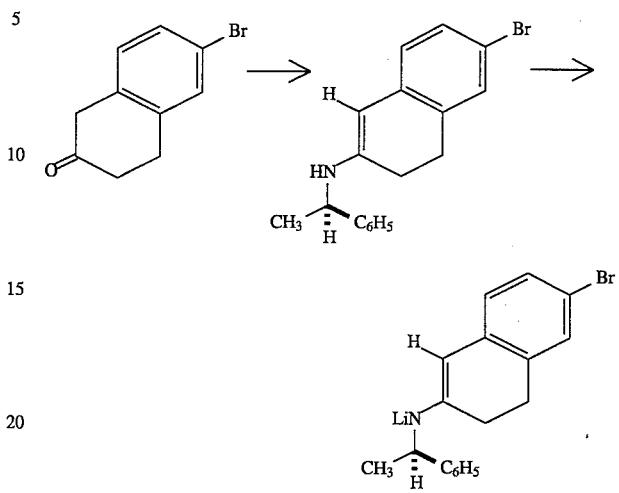

6-Bromo-2-tetralone, (45.0 g, 200 mmol uncorrected, potency of 90%, 0.90 equiv, corrected) was refluxed with (R)-(+)-phenethylamine (26.6 g, 220 mmol, 1.10 equiv, p-toluenesulfonic acid (160 mg, 0.84 mmol, 0.004 equiv), and toluene (600 mL) in a 2000-mL round bottom flask fitted with a water separator. Reflux was continued until a water-free distillate was observed and then approximately 250 mL of toluene was collected over about 2 to 3 hours. The mixture was cooled to approximately 30°–35° and concentrated under house vacuum.

The residue above, containing the enamine intermediate, was dissolved in tetrahydrofuran (THF, 480 g, 540 mL) and cooled below −50°. This solution of the enamine was added via cannula to a solution of lithium diisopropylamide (LDA, 1.15 equiv) at −50 to −60° over 5 minutes. The solution was warmed to −5° over 20 minutes and then recooled to −75° affording a 0.125 M solution of the lithium salt starting material. Proceed immediately to next step—unstable intermediate.

Example 1

(4aR)-10bR)-8-bromo-10b-methyl-1,2,3,4,4a,5,6,10b-octahydrobenzo[f]quinoline-3-one
Step A—Methyl Iodide

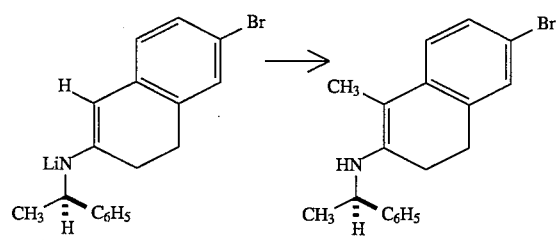

Methyl iodide (14.4 mL, 230 mmol, 1.15 equiv.) was added via syringe to the reaction mixture from Preparation 1 at −75° to −70° over 3 minutes. This solution was warmed to −5° in 20 minutes and then treated with methanesulfonic acid (24.8 g, 16.8 mL, 1.3 equiv.) affording a solution of the desired enamine admixed with diisopropylamine methanesulfonate as a slightly soluble, off-white precipitate, which was then removed by filtration.

Step B—Aza-Annulation

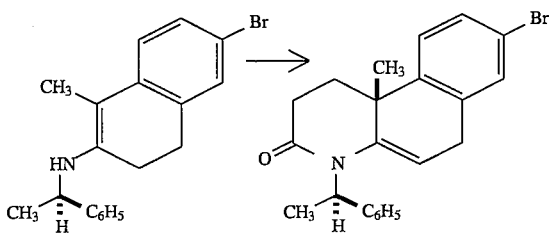

The reaction mixture solution from the above step was treated with acryloyl chloride (1.7 equiv.) at −75° in one portion over about 5 minutes. The mixture was then allowed to warm to −8° over 15 hours. The reaction was quenched by pouring into sodium bicarbonate (60 g in 240 mL of water at 5 to 7°, 15 minutes addition time, 20 minutes stir, pH should be basic). Dimethylaminopyridine (0.01 equiv, 2 mmol, 244 mg) was added and the mixture stirred another hour. The mixture was concentrated under vacuum (10°–25°, initial volume 2000 mL; final volume 400 mL) and methylene chloride (400 mL) was added and the organic phase was washed with aqueous sulfuric acid (1.0 N, two 100 mL portions, pH 1–3) and sodium bicarbonate (1.0 N, 50 mL, pH 9). The organic extracts were dried and clarified by filtration over approximately 20 g of 4Å molecular sieves. The mixture was concentrated under vacuum to a total weight of 129.6 g.

Step C—Reduction-Cleavage

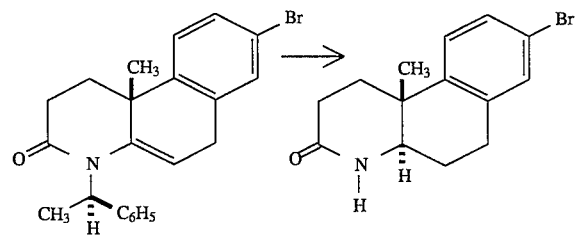

To about 103 g of the above residue were added 37 mL of triethylsilane and 46 mL of trifluoroacetic acid at 25°. After 1.5 hours reduction was approximately 50% complete. After an additional 12 hours the reduction was complete by TLC. The mixture was then refluxed for 2.5 hours. The mixture was allowed to cool and was concentrated in vacuo to approximately 25 g. The residue above was dissolved in 400 mL of methylene chloride, washed with aqueous sodium hydroxide (enough for pH 11), and concentrated under vacuum. This concentrate was then treated with diethyl ether (approximately 5 volumes at 22° then 0° for several hours). The mixture was filtered and rinsed with several small portions of ether affording the desired product after drying as a crystalline, white solid (yield=approximately 60% based on purity of bromotetralone).

Analysis by reverse phase high performance liquid chromatography on a Waters NOVA-PAK instrument, C-18 3.9×150 mm column, eluting with 2 ml/min. of 25% aqueous acetonitrile containing 1% ammonium acetate, operating the detector at 220 nm.

Potency: 91.2%

Related substances: 6.8%

Anal Calcd for $C_{14}H_{16}NOBr$:
C, 57.16; H, 5.48; N, 4.76; Br, 27.16

Found: C, 55.08; H, 5.43; N, 4:30; Br, 27.78

$^{13}C$ NMR (CDCl$_3$): 21.60, 24.62, 28.24, 29.48, 33.15, 36.90, 57.28, 121.03, 127.42, 130.09, 132.86, 137.51, 143.26, 173.62

1H NMR (CDCl$_3$): 1.18(s, 3H)

α589 nm - 90°

α365 nm - 302° ee% > 98%, determined by chromatography on a Chiracel-OD instrument and 1 mL/min, 40°, eluting with 10% isopropanol in hexane and operating the detector at 220 nm.

Preparation 2 Acrylic Anhydride

Two hundred fifty ml of tetrahydrofuran was added to a 1 liter jacketed flask with stir bar and nitrogen purge, and 250 mg of butylated hydroxytoluene, 250 mg of hydroquinone and 25.3 g of triethylamine were added. The solution was cooled to 0°, and to it was added 18.0 g of acrylic acid over a 2 minute period. The solution was cooled again to 0°, and 22.6 g of acryloyl chloride was added over a 10 minute period. It is important to maintain the addition rate constant during the acryloyl chloride addition. Maintaining the jacket temperature at 0° and continuing the nitrogen purge, the solution was stirred for 1 hour, and then it was filtered in a vacuum filter and the cake was washed with 50 ml of additional tetrahydrofuran.

Preparation 3

(R)-6-chloro-2-(1-phenylethylamino)-3,4-dihydronaphthalene, lithium salt

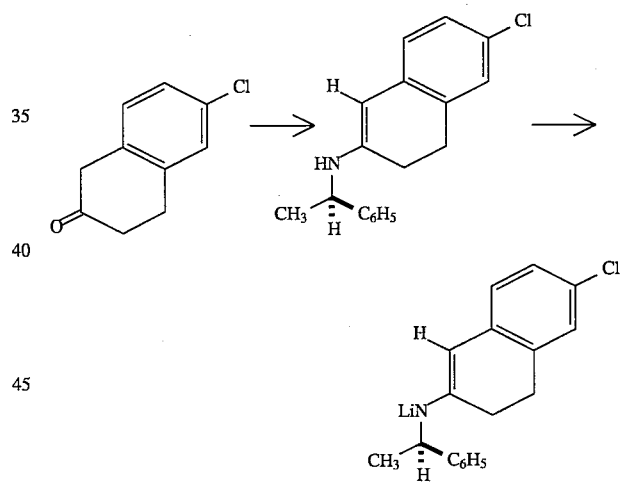

6-Chloro-2-tetralone (4.51 g, 25 mmol) was reacted with 3.32 g of (R)-(+)-phenethylamine and 20 mg of p-toluenesulfonic acid. The reaction was carried out as shown in Preparation 1 above in 100 mL of toluene, and when the reaction was complete the mixture was concentrated under vacuum and the residue was dissolved in 70 mL of tetrahydrofuran. The solution was cooled to −50 to −60°, and was added quickly to a solution of 1.15 equivalents of lithium diisopropylamide in 122 mL of tetrahydrofuran at −70° to −65°. The solution was allowed to warm to −20° for 20 minutes, and was then quickly recooled to −75°.

Example 2

(4aR)-(10bR)-8-chloro-10b-methyl-1,2,3,4,4a, 5,6,10b-octahydrobenzo[f]quinoline-3-one

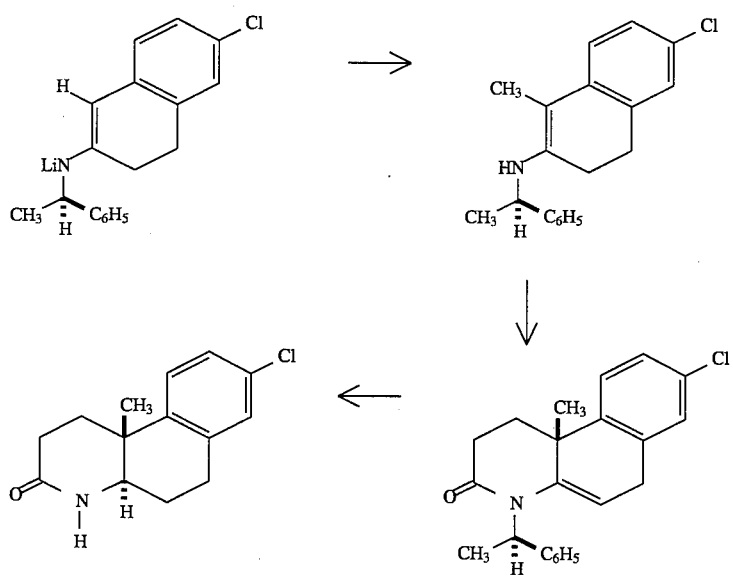

To the cold solution from preparation 3, was added 1.15 equivalents of methyl iodide, and the mixture was allowed to warm to −5° over a 15 minute period with continued good stirring. Then 1.3 equiv. of methanesulfonic acid was added to the mixture over a 5 minute period. That mixture was vigorously stirred for 10 minutes at −5°, and was then cooled again to −75°. To it was added in one portion, 2.4 equiv. of acrylic anhydride, with continued stirring, and the mixture was allowed to warm from −75° to 15° over a period of 13 hours.

The resulting reaction mixture was poured into a well stirred solution of aqueous sodium bicarbonate (2 g/200 mL at 20°) and 100 mg of dimethylaminopyridine. After two hours of stirring at ambient temperature, most of the volatiles were removed under vacuum, and 130 mL of methylene chloride was added. The mixture was washed with 50 mL of 1 N hydrochloric acid, and then with aqueous sodium bicarbonate, and the organic phase was dried and concentrated to a white foam (10.37 g).

The foam was placed in a flask in a ice bath and was treated with 40 mL triethylsilane and 60 mL of trifluoroacetic acid for 15 hours at 0° and was then held for four days at 25°. The volatiles were removed under vacuum, and the colorless oil was decanted from the solid product. The residue was dissolved in 200 mL of methylene chloride and washed with saturated aqueous sodium bicarbonate. The extracts were dried with 4A molecular sieves and evaporated. The residue was washed with 76 mL of diethyl ether to obtain 3.87 g of the desired product as a white solid admixed with a small amount of isomeric material.

MS=249, 251 (M+, M+2)

IR (CHCl$_3$)=3396, 1662 cm$^{-1}$.

Anal Calcd for C$_{14}$H$_{16}$NOCl:
C, 67.33; H, 6.46; N, 5.61; Cl, 14.20

Found: C, 66.57; H, 6.43; N, 5.40; Cl, 13.91

$^1$H NMR (CDCl$_3$ 500 MHz): 1.16(s, 3H), 3.54(dxd, 1H),

UV (MeOH): γ205 (21000), 271(600), 280(600)

Preparation 4

(R)-7-fluoro-2-(1-phenylethylamino)-3,4-dihydronaphthalene, lithium salt

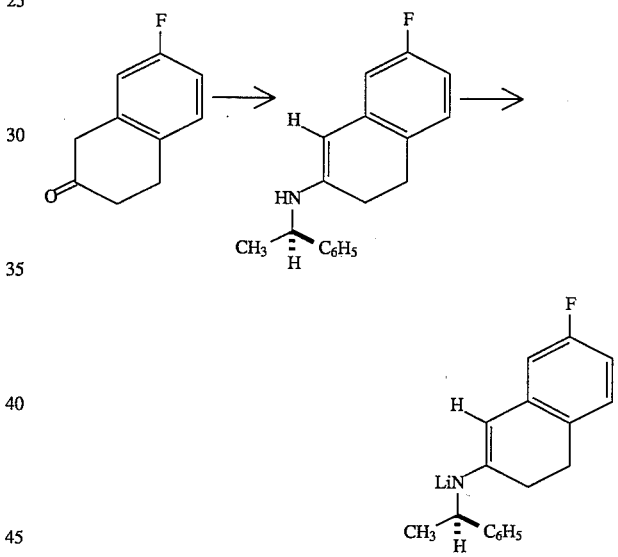

Five g of 7-fluoro-2-tetralone was reacted with 4.06 g of (R)-(+)-1-phenylethylamine in 75 mL of toluene in the presence of 25 mg of p-toluenesulfonic acid. The reaction was carried out under the conditions described in Example 1, and when the reaction was substantially complete, the toluene was distilled off and the mixture was concentrated under vacuum. Then 75 mL of anhydrous THF was added and the solution was cooled to −78° under nitrogen.

LDA was prepared by the addition of 21.9 mL of n-butyllithium to a solution of 3.54 g of diisopropylamine in 90 mL of anhydrous THF at −50 to −60°. The mixture was stirred for 30 minutes, and then the solution was cooled to −78°.

TO the LDA solution was added the cold solution of the first step reaction mixture, over a period of 30 minutes. Then the mixture was warmed to −20° and then recooled to −78°.

Example 3

(4aR)-(10bR)-9-fluoro-10b-methyl-1,2,3,4,4a, 5,6,10b-octahydrobenzo[f]quinoline-3-one

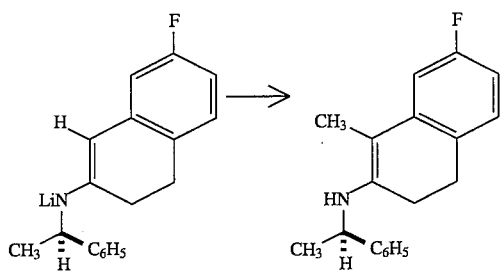

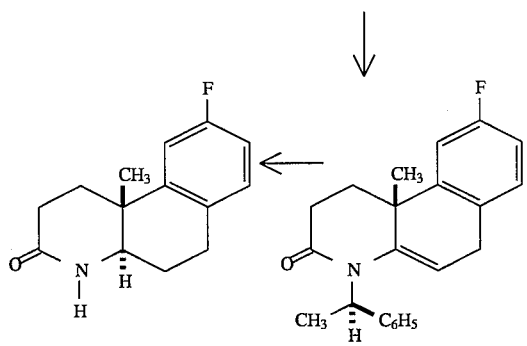

To the cold solution from Preparation 3 was added 5.0 g of methyl iodide, and the mixture was then warmed to 0° over 15 minutes. Then 2.6 mL of methanesulfonic acid was added slowly to the reaction mixture, and the mixture was recooled to −78°. Then 9.2 g of acrylic anhydride was added rapidly to the mixture, and the mixture was stirred for 15 hours while the temperature was allowed to slowly rise to the ambient temperature, maintaining a nitrogen atmosphere over the mixture at all times.

The reaction mixture was then quenched with 50 mL of saturated aqueous sodium bicarbonate solution, and the mixture was stirred for 30 minutes at ambient temperature. It was then extracted three times with 50 mL portions of saturated aqueous sodium chloride, and the organic layer was dried over sodium sulfate, filtered, and concentrated under high vacuum with a rotary evaporator.

To the residue were added 50 mL of triethylsilane, and 50 mL of trifluoroacetic acid at −10° in a flask equipped with a condenser. The mixture was stirred for 24 hours at −10°, and for 24 hours at 10°, and was then heated at the reflux temperature under nitrogen for 3 hours with continuous stirring. It was then cooled to ambient temperature. The mixture was concentrated under vacuum with a rotary evaporator, and the resulting oil was dissolved in 250 mL of dichloromethane. The solution was extracted three times with 75 mL portions of saturated aqueous sodium bicarbonate, and was dried over sodium sulfate, filtered, and concentrated under vacuum. The residue was partially purified by liquid phase chromatography, using a gradient solvent from 3/1 ethyl acetate/hexanes to 100% ethyl acetate. The product-containing fractions were concentrated under vacuum, and the residue was crystallized from ethyl acetate/ hexanes. The crystalline product was isolated and dried in a vacuum oven, to obtain 3.53 g of the desired product, 50% yield, m.p. 187.9°.

Analysis calculated for $C_{14}H_{16}NOF$: C, 72.08; H, 6.91; N, 6.00

Found: C, 72.31; H, 7.08; N, 5.99

We claim:

1. A process for preparing a compound of the formula

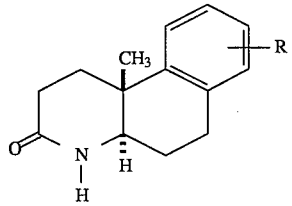

I wherein R is hydrogen, methylthio, chloro, bromo or fluoro, and is located at the 7-, 8- or 9-position; comprising reacting a compound of the formula

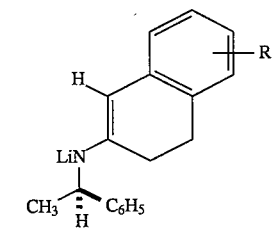

II with methyl iodide in an ether solvent to prepare a compound of the formula

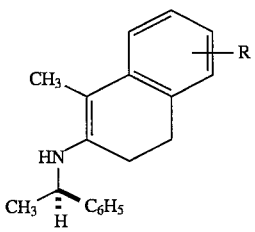

III combining acrylic anhydride or acryloyl chloride with the reaction mixture comprising the compound of formula III to prepare a compound of the formula

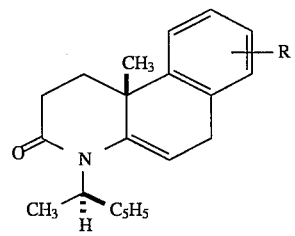

IV quenching the reaction with sodium bicarbonate, evaporating the organic solution comprising the compound of formula IV;

and combining the residue comprising the compound of formula IV with a trialkylsilane and trifluoroacetic acid in the absence of a solvent to prepare the compound of formula I.

2. A process of claim 1 wherein the compound of formula II is supplied as a reaction mixture containing residual diisopropylamine.

3. A process of claim 1 wherein the compound of formula I is a compound wherein R is at the 8-position.

4. A process of claim 2 wherein the reaction mixture from the methyl iodide step is further treated with methanesulfonic acid.

5. A process of claim 1 wherein the compound of formula III is reacted with acrylic anhydride.

6. A process of claim 3 wherein the compound of formula I is a compound wherein R is methylthio, bromo or chloro.

7. A process of claim 6 wherein the compound of formula III is reacted with acrylic anhydride.

8. A process of claim 3 wherein the compound of formula II is supplied as a reaction mixture containing residual diisopropylamine, and the reaction mixture from the methyl iodide step is further treated with methanesulfonic acid.

9. A process of claim 8 wherein the compound of formula III is reacted with acrylic anhydride.

10. A process of claim 9 wherein the compound of formula I is a compound wherein R represents bromo or chloro.

11. A process of claim 1 wherein the methyl iodide step is carried out at a temperature from about −80° to about −60°.

12. A process of claim 5 wherein the acrylic anhydride step is carried out at from about −100° to about −70°, warming to a temperature from about −20° to about 20°.

13. A process of claim 1 wherein the reaction mixture from the acrylic anhydride or acryloyl chloride step is quenched with solid sodium bicarbonate.

14. A process of claim 5 wherein the reaction from the acrylic anhydride step is quenched with solid sodium bicarbonate.

15. A process of claim 10 wherein the reaction from the acrylic anhydride step is quenched with solid sodium bicarbonate.

* * * * *